United States Patent Office

PTO - BOYERS, PA Duty Station

MISSING PAGE TEMPORARY NOTICE

PATENT # PP3380 FOR ISSUE DATE 7-31-73

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # All Draw.

Data Conversion Operation

Boyers, Pa

United States Patent Office

Plant Pat. 3,380
Patented July 31, 1973

3,380
ROSE PLANT

Reimer Kordes, Sparrieshoop, Germany, assignor to Jackson & Perkins Company, Medford, Oreg.

Filed Oct. 15, 1971, Ser. No. 189,679
Int. Cl. A01h *5/00*
U.S. Cl. Plt.—25 1 Claim

This invention relates to a new and distinct variety of rose plant of the floribunda class originated by me by crossing the variety Zorina, U.S. Plant Patent 2,321 by the variety Konigen der Rosen, unpatented.

The primary objective of this breeding was to produce a new and improved variety of the floribunda class bearing flowers similar to Zorina but having a deeper, more intense color with flower form and keeping quality as good or better than Zorina.

This objective was fully achieved along with other desirable improvements as evidenced by the following unique combination of characteristics which are outstanding in the new variety and which distinguish it from its parents, as well as from all other varieties of which I am aware:

(1) When grown outside, a vigorous, fully branched upright floribunda plant habit.

(2) A flower form similar to Zorina in the open stages but slightly shorter in the bud stage.

(3) Bud and flower color dominantly Capsicum Red on the upper surface of petals and Dutch Vermilion on the reverse side.

(4) Little or no fragrance.

(5) A stiff habit of growth.

(6) A stiffness of petals in open form causing flowers to hold form very long.

Asexual reproduction of this new variety by budding as performed at Wasco, Calif. shows that the aforementioned characteristics come true to form and are established and transmitted through succeeding propagations.

The accompanying drawing shows typical specimens of the vegetative growth and flowers of this new variety in different stages of development and as depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
- *Seed parent.*—Zorina, U.S. Plant Patent 2,321.
- *Pollen parent.*—Konigen der Rosen.

Classification:
- *Botanic.*—Rosa hybrid
- *Commercial.*—Floribunda

*Flower*

Observations were made in early August in the afternoon at Irvine, Calif.

Blooming habit: Recurrent—continuous.

Bud:
- *Size.*—Medium, ¾"–⅞" when sepals first divide.
- *Form.*—Short with flat top.
- *Color.*—When sepals first divide close to Signal Red (719)—most of petal. Large area at base, lower side is greenish yellow, difficult to match because of small size but very close to Uranium Green (63/2). When half blown; inside of petals Capsicum Red (715). Large area (about 3/16" diameter) is Lemon Yellow (4/1) at base of petal; reverse of petals Dutch Vermilion (717/2). Yellowish base is larger than on upper side (close to ¼") and is close to Uranium Green (63/1).

- *Sepals.*—Color: outer surface—Pod Green (061/1) in center area, Pod Green (061) along outer edges—numerous gland-like hairs on outer surface. Inner surface—Pod Green (061/1), lightly covered with white tomentum. Three appendaged sepals normally appendaged. Two unappendaged sepals hairy edged.
- *Receptacle.*—Color: Pod Green (061). Shape: receptacle is only an enlargement of the stem—about twice the diameter of stem. Size: small, slender. Surface: smooth.
- *Peduncle.*—Length: medium. Surface: prickly. Color: Pod Green (061). Strength: stiff, erect.
- *Opening.*—Slowly opens, outer petals curl under slightly giving pointed shape to petals. Center exposed in fully open stage.

Bloom:
- *Size.*—Medium. Average size when fully expanded, 3".
- *Borne.*—Singly, in clusters, flat.
- *Stems.*—Long; generally very stiff, erect, strong.
- *Form.*—When first open, high center. Permanence—outer petal edges slightly curled and shows center when fully open.
- *Petalage.*—22 petals under normal conditions.
- *Color.*—Center of flower: upper side of petals—outer area Fire Red (15) gradually blending toward center of petal to Nasturtium Red (14). Base of petal Lemon Yellow (4/1). Reverse side of petals—Capsicum Red (715/3). Outer petals: upper side of petals same as center petals; reverse of petals same as center petals. Base of petals—upper side of petal Lemon Yellow (4/1); reverse side of petal near Uranium Green (63/1). General tonality from a distance—Capsicum Red (715) when half to full open.
- *Discoloration.*—General tonality at end of first day—Capsicum Red (715/3). Third day—Scarlet (19).
- *Fragrance.*—None.

Petals:
- *Texture.*—Thick, very rigid.
- *Surface.*—Inside—satiny. Reverse—satiny.
- *Shape.*—Near round.
- *Form.*—Edges slightly quilled.
- *Arrangement.*—Imbricated.
- *Petaloids in center.*—Few to none.
- *Persistance.*—Drop off cleanly.
- *Lastingness.*—On the plant—very long. As cut flower—very long.

Reproductive parts:
- *Stamens, anthers.*—Large. Color—near rose red with prominent golden yellow borders. Arrangement—regular around styles.
- *Stamens, filaments (threads).*—Medium. Color—yellow.
- *Pollen.*—Color—gold yellow.
- *Styles.*—Loosely separated, of medium length. Color—white at base to near light purple near stigmas.
- *Stigmas.*—Color—yellow.
- *Ovaries.*—All enclosed in calyx.

*Plant*

Form: Bush.

Growth: Very vigorous, upright, branching.

Foliage: Number of leaflets on normal mid-stem leaves, 5.
- *Size.*—Large.
- *Quanity.*—Abundant.
- *Color.*—New foliage: lower surface—Purple Madder (1028). Upper surface—Garnet Brown (00918/3). Old foliage: darker than Spinach Green (0960) when well fertilized.

Leaflets:

*Shape.*—Oval pointed.

*Texture.*—Upper side—leathery. Under side—smooth. Ribs and veins—prominent on underside.

*Edge.*—Serrated.

*Serration.*—Double, large.

*Petiole.*—Rachis—color underside—green; upperside—reddish. Underside—prickles.

*Stipules.*—Long; edge is very glandular.

*Disease resistance.*—Resistant to mildew under normal growing conditions at Irvine, Calif.

Wood:

*New Wood.*—Color—light green. Bark—smooth.

*Old Wood.*—Color—green. Bark—smooth.

Thorns:

*Quantity.*—On main stalks from base—many; on laterals from stalk—many.

*Form.*—Broad base; long, straight, angled downward slightly.

*Color when young.*—Translucent rose pink, basal half; light green tips.

*Position.*—Irregular.

Prickles:

*Quantity.*—On main stalks—many; on laterals—many.

*Color.*—Reddish.

I claim:

1. A new and distinct variety of rose plant of the floribunda class, substantially as herein shown and described, characterized particularly as to novelty by the unique combination of a tall, well branched plant with relatively stiff stems, freely borne flowers of Capsicum Red (reverse of petals Dutch Vermilion), long lasting flowers, thorny stems and foliage relatively mildew free.

No references cited.

ROBERT E. BAGWILL, Primary Examiner